United States Patent [19]

McMurry et al.

[11] Patent Number: 4,939,254

[45] Date of Patent: Jul. 3, 1990

[54] TEMPLATE SYNTHESIS OF MACROCYCLIC CATECHOLAMIDE COMPLEXES

[75] Inventors: Thomas J. McMurry, Rockville, Md.; Kenneth N. Raymond, Berkeley, Calif.

[73] Assignee: The Regents of the University of California, Oakland, Calif.

[21] Appl. No.: 400,360

[22] Filed: Aug. 30, 1989

Related U.S. Application Data

[63] Continuation of Ser. No. 186,466, Apr. 26, 1988, abandoned.

[51] Int. Cl.$^5$ ................. C07D 487/18; A61K 31/395
[52] U.S. Cl. .................................... 540/452; 514/184; 514/185; 514/186; 422/2; 422/9; 330/299
[58] Field of Search .......................................... 540/452

[56] References Cited

U.S. PATENT DOCUMENTS 4,702,998 10/1987 Tanaka et al. ...................... 540/452

OTHER PUBLICATIONS

Hosseini, M. W. et al., "Synthesis of Cage-Type Iron Sequestering Agents", XI International Symposium on Macrocyclic Chemistry, Florence, Italy, Sep. 1–4, 1986.
Kiggen, W. et al., *Angew. Chem Inter. Ed. Eng.* (1984), 23, 714.
McMurry, T. J. et al., "Macrobicyclic Iron (III) Sequestering Agents", *J. Am. Chem. Soc.*, 109, 7196 (1987).
Rodgers, S. J. et al., "Ferric Iron Sequestering Agents", 15, Synthesis, Solution Chemistry, and Electrochemistry of a New Cationic Analogue of Enterobactin, *Inorganic Chem.*, 26, 1622 (1987).
McMurry, T. J. et al., "Template and Stepwise Syntheses of a Macrobicyclic Catechoylamide Ferric Iron Sequestering Agent", *JACS*, 109, 3451 (1987).

*Primary Examiner*—Robert T. Bond
*Attorney, Agent, or Firm*—Flehr, Hohbach, Test, Albritton & Herbert

[57] ABSTRACT

A method is provided for a high yield template synthesis of macrocyclic catecholamide ligands.

2 Claims, No Drawings

TEMPLATE SYNTHESIS OF MACROCYCLIC CATECHOLAMIDE COMPLEXES

This invention was made with Government support under Grant Nos. AM-32999 and HL-07067 awarded by DHHS. The Government has certain rights in this invention.

This is a continuation, of application Ser. No. 186,466 filed 4/26/88 abandoned.

The present invention is directed to a method for preparing macrocyclic catecholamide complexes which are made by a template reaction wherein key starting materials and intermediates are held in an optimum configuration for cyclization as ligands in a metal complex.

BACKGROUND OF THE INVENTION

Macrobicyclic ligand systems are known in polyether complexing agents and polyamines. However, until the synthesis of macrocyclic compounds incorporating catechol binding subunits, very few other macrobicyclic ligands, particularly those designed to complex Fe (III) or other high-valent transition metals, have been made. Macrocyclic ligands incorporating catechol binding subunits have been made by high-dilution methods, high-dilution being required to favor intramolecular reactions (i.e., cyclization), rather than non-ring forming intermolecular reactions. For example, Kiggen, et al., *Ang. Chem. Int. Ed. (Eng.)*, 23, 714 (1984) disclose synthesis of oligocyclic cavities containing two or three catechol subunits made by high-dilution methods. However, the yields for the macrocyclic compounds using high-dilution methods are typically extremely low, usually about 20% or much less. These methods also suffer from the disadvantage of requiring at least one step under high-dilution conditions requiring a large volume of solvent. This impairs the applicability of the high-dilution process for rapid and commercially feasible processes.

Furthermore, the high-dilution methods usually require multiple step syntheses whereby intermediates are collected and transferred to different vessels for further reaction due to the diversity of conditions required for each step.

It is thus an object of the present invention to provide a novel method for making macrocyclic catecholamides by a template reaction utilizing metal chelates whereby cyclization reactions may be conducted in a single vessel with advantageously high yields of the macrocyclic compound.

These and other objects will be apparent from the following description and appended claims and from practice of the present invention.

SUMMARY OF THE INVENTION

The present invention provides a method for making compounds of the formula Ia, Ib or Ic

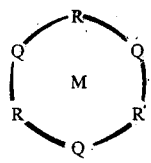

(Ia)

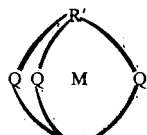

(Ib)

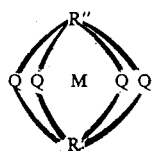

(Ic)

wherein M is a hexadentate or octadentate metal ion, Q is a catechol moiety as defined hereinbelow, and R, R' and R" are amine-capping moieties. Generally, the present invention is directed to a method comprising the steps of reacting an activated ester or other activated reactive carboxyl derivative of a catechol dicarboxylate with a metal ion to form a metal complex whereby the catechol ligands are held in a desired orientation around the metal ion, then reacting the complex with two equivalents of an amine-capping compound, or, alternatively, with one equivalent each of two different amine-capping compounds, to form the macrocyclic compound. In some instances, the capping reaction will not go to completion under conditions of the capping reaction, thus requiring a subsequent treatment with a weak basic hydrolyzing agent to complete the cyclization between each amine group of the capping reagent and the activated ester on the catechol.

DESCRIPTION OF THE PREFERRED EMBODIMENTS

The present invention is directed to a method of making compounds of the formula Ia, Ib or Ic above wherein each group Q is independently

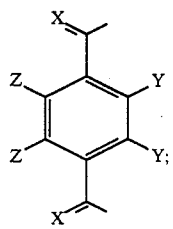

wherein X is oxygen or sulfur; Y is $-OR_1$ or $-SR_1$; $R_1$ is hydrogen, alkyl of 1-4 carbon atoms, a hydroxy or mercapto protecting group, including, but not limited to silyl, benzyl and borate protecting groups, Z is hydrogen, alkyl of 1-4 carbon atoms; $-SO_3H$, $-NO_2$, $-CO_2R_1$, or halo; and each R is independently $-(NHCH_2-(T)-CH_2NH)-$ wherein T is $-(CH_2)_n-$, $-(CH_2)_nN-(CH_2)_n-$, OR

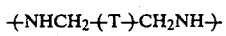

$(CH_2)_nCH_3$; each R' is independently $-[N-H-(CH_2)_n]_3N$

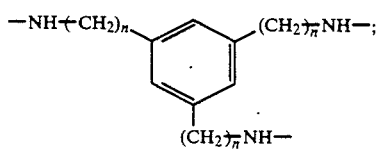

and each R″ is independently $C[(CH_2)_n NH]_4$;

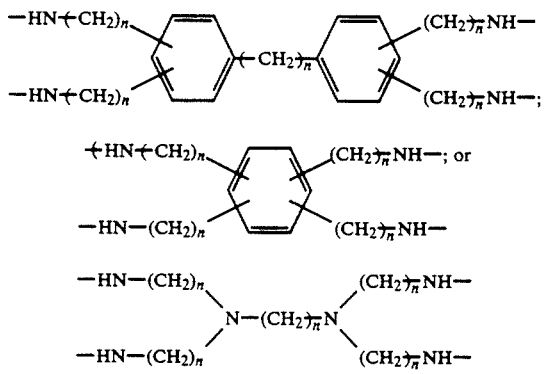

and each n is independently an integer from 0 to 6.

One of the starting materials for the method according to the present invention is an activated ester or imide of a catechol derivative of the formula II:

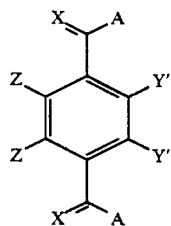

wherein Z and X are as defined above; Y' is —OH or —SH; and —CXA is an activated ester or imide. The catechol (II) will be treated with a metal salt, MB, wherein M is a hexadentate or octadentate metal ion and B is its counter ion, to form a metal complex of the formula III:

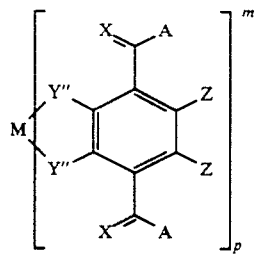

wherein Y″ is oxygen or sulfur; X, A and Z are as defined above, m is positive or negative integer or zero integer from −6 to +6, p is an integer of 3 or 4.

The metal complex (III) may then be capped with amine groups of the formula H-R-H, R'H$_3$, and/or R″H$_4$. If all of the capping groups are to be identical, then the appropriate number of equivalents of the desired capping group may be reacted with the complex III. That is, if the compound of the formula Ia is to be made then three equivalents of the capping group RH$_2$ will be reacted with one equivalent of the complex III. If compounds of the formula Ib or Ic are to be made then two equivalents of the capping group R'H$_3$ or R″H$_4$, respectively, are treated with one equivalent of the metal complex III. In some instances, one or more amines of the capping groups will remain free after the capping reaction, perhaps due to the internal stress of the macrocyclic rings.

In such instances, a final step of treating the remaining uncyclized activated ester(s) on the catechol with an acylation catalyst or acylation promoting agent will complete the cyclization. In some instances this final step will not be required if the length of the capping groups is sufficient so that the esters and amines may react without treatment under more stringent conditions.

In some instances it will be desirable to have different capping groups, for example, such as in the formula (Ib) where the two R' groups are different from each other. To form compounds of that nature, one equivalent of the metal chelate (III) will be reacted with one equivalent of one of the desired capping groups, then one equivalent of the second capping group will be added. As described above, in some instances one or more of the free terminal amine of the capping groups will not go to completion under conditions of the capping reaction and subsequent treatment with an acylation catalyst or acylation promoting agent may be needed to complete the cyclization.

As produced by the above method, the compounds Ia, Ib and Ic are metal chelates and are useful as metal sequestering agents, particularly for iron and actinide decorporation agents which remove metal ions from in vivo environments. The metal ion, M, may be removed from the ligand cage by treatment with an excess of another chelator, such as, EDTA, and separation of the chelated species by chromatography, including, TLC, HPLC, etc.

Particularly preferred capping groups for their in vivo distribution properties of the ligand are those in which the capping group, R, R' or R″ contains at least one tertiary amine group. The capping groups themselves, may be prepared by conventional methods.

In a preferred embodiment, the 2,3-dihydroxy terephthalate activated ester (compound of the formula II wherein Z is hydrogen, Y' is OH and CXA is a carboxy succinimide) is treated with anhydrous ferric chloride in a polar aprotic solvent, such as dimethylformamide, to degenerate the ferric tris (catecholate) compound. (Formula III, p=3 and m is −3). A subsequent reaction with a capping group, such as tris (2-aminoethyl) amine at room temperature for about 14 hours forms the following complex:

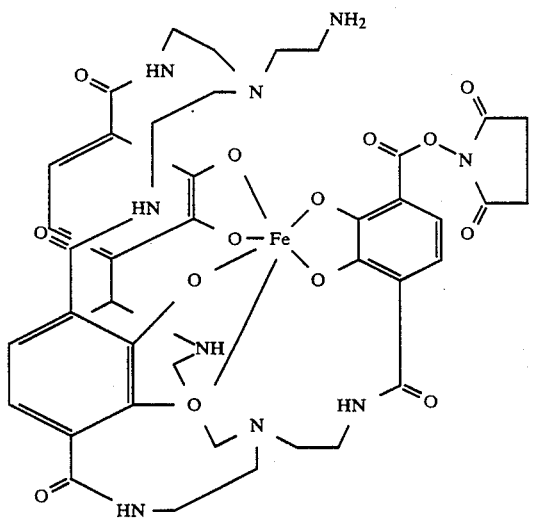

wherein all but one of the activated ester groups has been cyclized with a free amine group of the capping moiety. Two equivalents of the capping reagent are added to form this intermediate and it is obtained in about a 70% yield. To close the final ring, a weak basic hydrolyzing agent such as 4-dimethylaminopyridine is added and the mixture is heated to about 65° C. resulting in a 50% overall yield of the macrobicyclic complex having the following structure

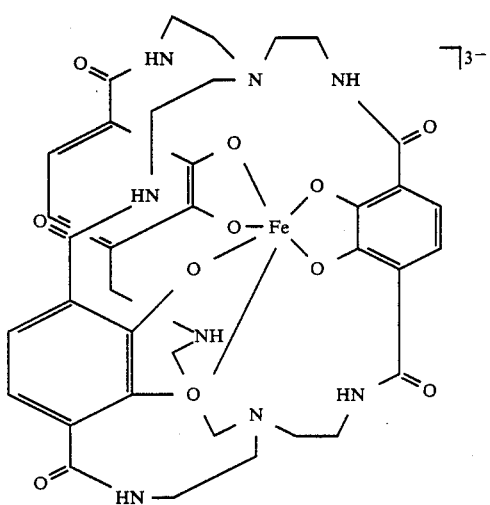

As an alternate and preferred embodiment, if the intermediate:

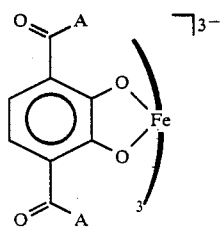

is reacted with only one equivalent of tris (2-aminoethyl(amine)) the following intermediate is formed:

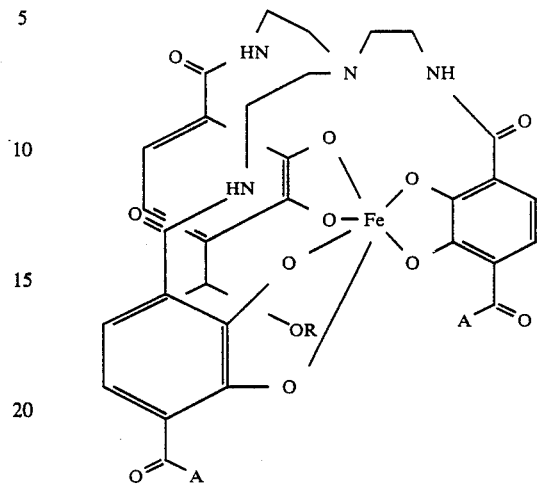

then treatment with a second capping agent such as, 1,3,5-tri(aminomethyl)benzene leads to the following complex having two different capping groups

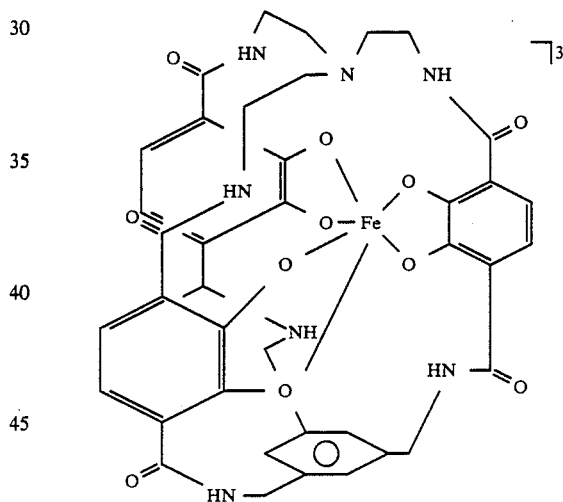

agents for transition metal ions, such as iron (III) and iron (II), aluminum (III), Ga (III), Ti (IV) as well as for the actinides. Particularly when the capping group contains a tertiary amino group which may be protonated to render the complex water soluble or more readily water soluble, the complexes according to the present invention are useful for in vivo applications. For example, the complexes according to the present invention may be utilized to detoxify (i.e. decorporate) a subject of metal ions by complexing the ions in vivo, which are then excreted. In addition, complexes of the invention wherein the metal ion is a radiopharmaceutical agent, such as gallium (III), may be formed so that the complexes themselves are useful radiopharmaceuticals. Complexes of the invention wherein the metal ion is ferric ion, or other high-spin ion, may be similarly used as image enhancement agents for in vivo magnetic resonance imaging.

EXAMPLE

Dimethyl-2,3-dihydroxyterephthalate was reacted in acetone for 72 hours with benzyl chloride, potassium iodide and potassium carbonate (yield 85%); then converted to a salt under reflux in NaOH, DME/water for 9 hours (94%). The product was converted to the hydroxy-succinimide activated ester by treatment with N-hydroxysuccinimide, DCC in dioxane (yield 72%), followed by hydrogenation over 5% Pd-C in ethyl acetate at room temperature for one hour (yield approximately 100%). The resultant diester catechol was treated with ferric chloride and triethylamine in DMF; followed by addition of tris(2-aminoethyl) amine (2 equiv.) at room temperature for 14 hours, to form the bicapped ferric complex with one free amino group and one free ester. The final amide is formed by treatment with 4-dimethylaminopyridine at 65° C. for 5 days (70%) yield). The complex may be demetalized by treatment with a 10-fold excess of EDTA at pH 3.7, followed by purification by HPLC (linear elution of aqueous 0.01M acetic acid to 0.01 acetic acid in methanol).

It will be appreciated that various improvements and modifications of the invention will be apparent from the foregoing description and appended claims which are within the spirit and scope of the present invention. The invention is not deemed to be limited except by the scope of the following claims.

We claim:

1. A method for making a compound of a formula selected from the group consisting of Ia, Ib and Ic

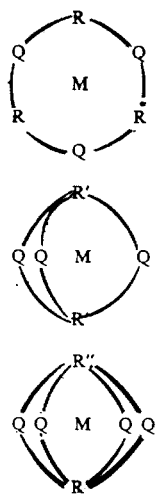

(Ia)

(Ib)

(Ic)

wherein each Q is independently

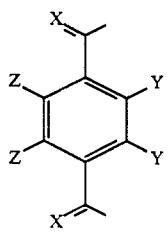

wherein
X is oxygen or sulfur, Y is $OR_1$ or $SR_1$; $R_1$ is hydrogen, alkyl of 1-4 carbon atoms or a hydroxy or mercapto protecting group, Z is hydrogen, alkyl of 1-4 carbon atoms, $SO_3H$, $NO_2$, $CO_2R_1$ or halo; each R is independently

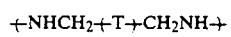

wherein T is $(CH_2)_n$, $-(CH_2)_nN-CH_2)_n$,

$(CH_2)_nCH_3$ each R' is independently

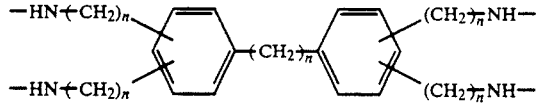

each R'' is independently

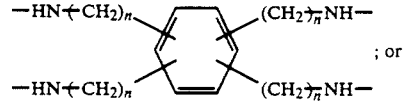

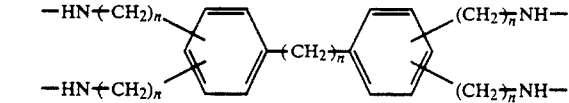

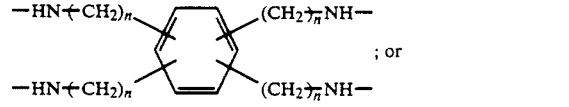

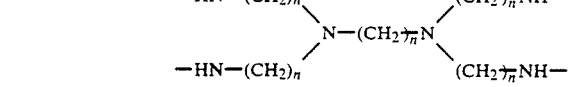

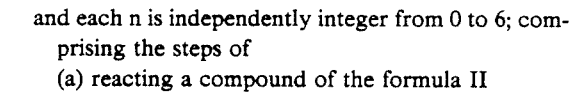

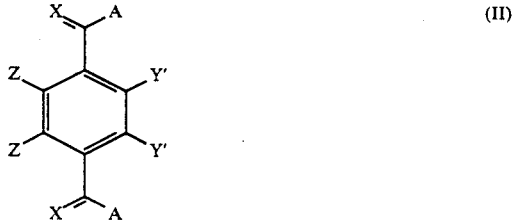

and each n is independently integer from 0 to 6; comprising the steps of
(a) reacting a compound of the formula II

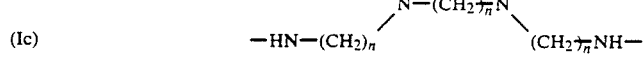

(II)

wherein Z and X are as defined hereinabove; Y' is OH or SH; and —CXA is an activated ester, imide or acid halide; with a metal salt, MB, perform a metal chelate of the formula III

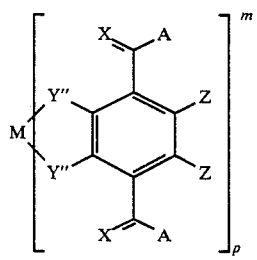

wherein Y" is oxygen or sulfur; MB is the metal salt of a hexadentate or octadentate metal ion and a counter ion B; X, A and Z are as defined hereinabove, m is a positive or negative integer or 0 from −6 to +6, p is a positive integer of 3 or 4;

(b) reacting one equivalent of said compound of formula III with two equivalents of a compound selected from the group consisting of $RH_2$, $R'H_3$ and $R''H_4$; to form compounds of the formula Ia, Ib or Ic or partially uncyclized intermediates thereto;

(c) optionally treating said intermediates from step (b), if present, with an acylation catalyst or acylation promoting agent to complete the cyclization of said intermediates to form compounds of the formula Ia, Ib or Ic.

2. A method for making a compound of the formula selected from the group consisting of Ia, Ib and Ic

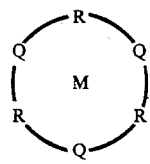 (Ia)

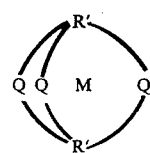 (Ib)

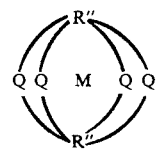 (Ic)

wherein
each Q is independently

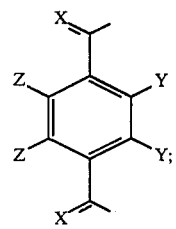

X is oxygen or sulfur; Y is $OR_1$ or $SR_1$; $R_1$ is hydrogen or alkyl of 1-4 carbon atoms; Z is hydrogen, alkyl of 1-4 carbon atoms, $SO_3H$, $NO_2$, $CO_2R_1$ or halo;

each R is independently

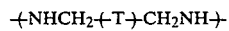

wherein T is 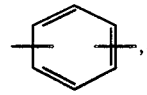, or

$(CH_2)_{\overline{n}}CH_3$ each R' is independently

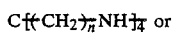 or

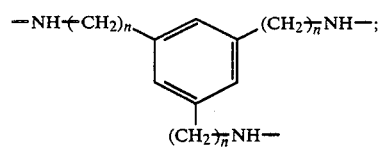

each R" is independently $C\{(CH_2)_{\overline{n}}NH\}_4$ or

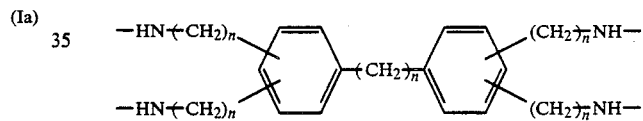

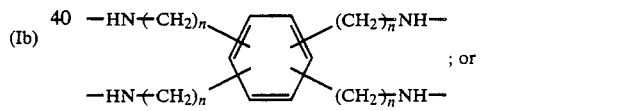 ; or

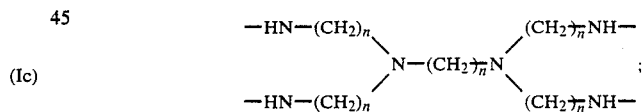

and each n is independently an integer from 0 to 6;

(a) reacting a compound of the formula II

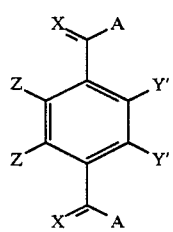 (II)

wherein Z and X are as defined hereinabove; Y' is OH or SH; and CXA is an activated ester, imide or acid halide; with a metal salt, MB to form a metal chelate of the formula III

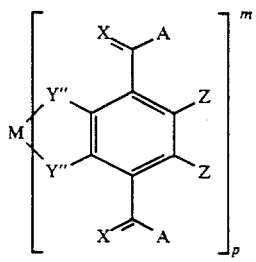

wherein Y″ is oxygen or sulfur; MB is the metal salt of a hexadentate or octadentate metal ion and a counter ion B; X, A and Z are as defined hereinabove, m is a positive or negative integer or 0 from −6 to +6, and p is an integer of 3 or 4;

(b) reacting one equivalent of said compound of the formula III with one equivalent of a first compound selected from the group consisting of $RH_2$, $R'H_3$ and $R''H_4$; to form a monocapped intermediate;

(c) treating said monocapped intermediate from step (b) with one equivalent of a second compound selected from the group consisting of $RH_2$, $R'H_3$ and $R''H_4$, with the proviso that said second compound is not the same as said first compound; to form compounds of the formulas Ia, Ib or Ic, or partially uncyclized intermediates thereto;

(d) optionally treating said intermediates from step (c), if present, with a weak basic hydrolyzing agent to complete the cyclization of said intermediates to form compounds of the formulas Ia, Ib or Ic.

* * * * *